(12) United States Patent
Vogler

(10) Patent No.: US 8,740,890 B2
(45) Date of Patent: Jun. 3, 2014

(54) SYSTEMS AND HAND PIECES FOR USE IN OPHTHALMOLOGY OR DERMATOLOGY

(75) Inventor: Klaus Vogler, Eckental (DE)

(73) Assignee: WaveLight AG, Erlangen (DE)

( * ) Notice: Subject to any disclaimer, the term of this patent is extended or adjusted under 35 U.S.C. 154(b) by 1589 days.

(21) Appl. No.: 12/323,616

(22) Filed: Nov. 26, 2008

(65) Prior Publication Data
US 2010/0130968 A1   May 27, 2010

(51) Int. Cl.
*A61B 18/18* (2006.01)
(52) U.S. Cl.
USPC ........................................... 606/10
(58) Field of Classification Search
USPC ................ 606/5, 9, 3, 4, 13, 6, 10, 11, 12
See application file for complete search history.

(56) References Cited

U.S. PATENT DOCUMENTS

| 5,656,186 A | 8/1997 | Mourou | |
| 2004/0243112 A1* | 12/2004 | Bendett et al. | 606/5 |
| 2004/0254568 A1* | 12/2004 | Rathjen | 606/4 |
| 2005/0171516 A1* | 8/2005 | Stoltz et al. | 606/9 |
| 2005/0259933 A1* | 11/2005 | Temelkuran et al. | 385/123 |

FOREIGN PATENT DOCUMENTS

EP   1486185   12/2004

OTHER PUBLICATIONS

European Patent Office, ISA, International Search Report for PCT/EP2008/010032, Mailing date Oct. 5, 2009, 4 pages.

* cited by examiner

*Primary Examiner* — Tuan V Nguyen
*Assistant Examiner* — Tin Nguyen
(74) *Attorney, Agent, or Firm* — Haynes and Boone, LLP

(57) ABSTRACT

The invention relates to a system for ophthalmology or dermatology, having a laser unit for generating pulsed laser radiation, the pulse length of the laser pulses lying in the femtosecond range, a hand unit for emitting laser radiation generated by the laser unit, and a flexible light waveguide for delivering the laser radiation generated by the laser unit to the hand unit. The invention furthermore relates to a corresponding hand unit for emitting pulsed laser radiation generated by a laser unit, the laser radiation having pulse lengths in the femtosecond range.

16 Claims, 2 Drawing Sheets

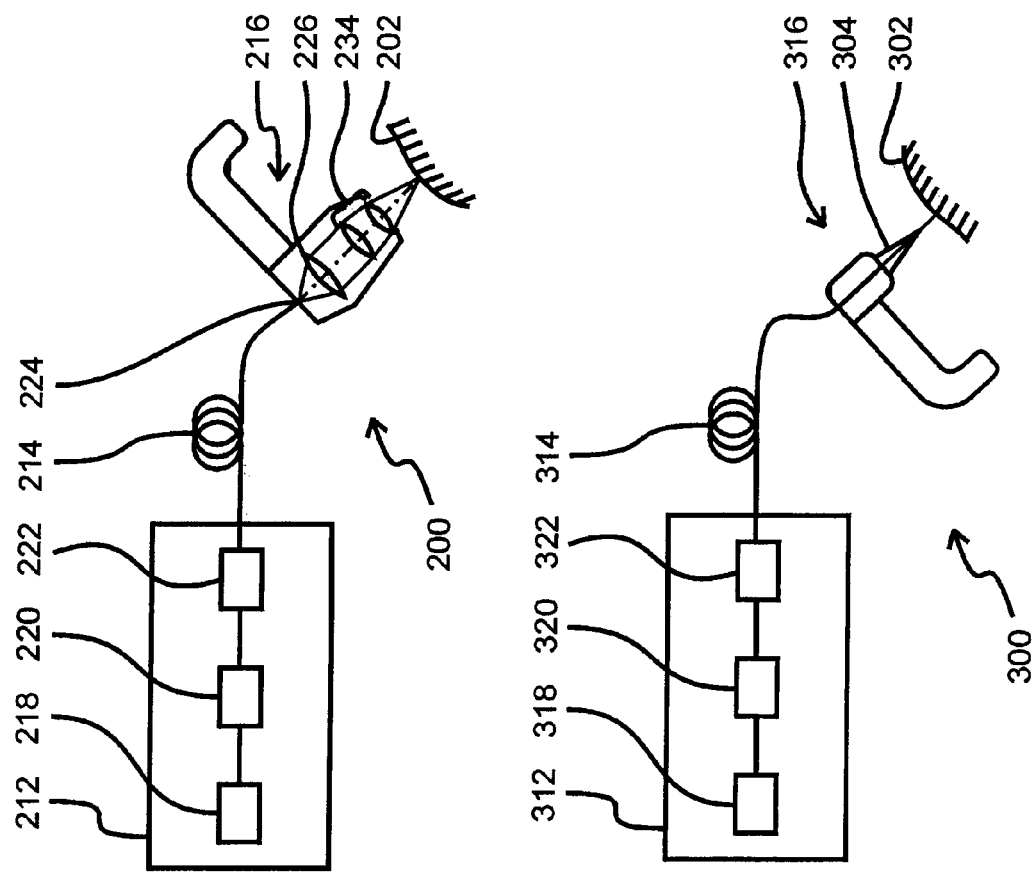

SYSTEMS AND HAND PIECES FOR USE IN OPHTHALMOLOGY OR DERMATOLOGY

TECHNOLOGICAL FIELD

The invention relates to a system for ophthalmology or dermatology, as well as to a and unit for emitting pulsed laser radiation.

BACKGROUND

In refractive opthalmological surgery, the refractive properties of a patient's eye are modified by interventions on the eye in order to correct defective vision. In particular the so-called LASIK method (LASer In Situ Keratomileusis) is known, in which the patient's cornea is reshaped. According to the conventional LASIK method, a flat corneal incision is made in a first microsurgical operation step with a mechanical instrument, usually a microkeratome. This creates a so-called "flap", which can be folded away so that underlying corneal tissue (stroma) is exposed. In the subsequent part of the LASIK operation, a particular ablation pattern is removed from the stroma. The flap is then folded back into place and heals relatively rapidly again with the remaining stroma. The conventional mechanical microkeratome uses a sharp, rapidly oscillating blade.

Recently, the microkeratome has been replaced by a laser, in particular a femtosecond laser, which makes the aforementioned flat incision in the cornea. The laser is focused onto a plane below the surface of the cornea, and is guided on a path which produces the flap in the same way as the microkeratome does. The extremely short laser pulses used for this, in the femtosecond range, have such high powers that, with a suitable focusing, it is possible to cut without causing internal heating effects or the like by utilising the so-called photodisruptive effect. Compared with the conventional mechanical microkeratome, higher accuracy and better reproducibility of the LASIK cuts are generally obtained.

In order to produce the flap by means of a laser, the patient is first positioned below the femtosecond laser. As for the conventional production of a flap by means of a microkeratome, a fixation ring, which is usually fixed by means of suction, is placed onto the eye. A contact glass, which touches the surface of the cornea and flattens it for maximally accurate production of the corneal incision by exerting a certain pressure, is then placed into the suction ring. A usually conical contact device is then connected to the actual femtosecond laser instrument. This is usually done so that the part of the laser instrument, which emits the laser radiation, is moved with the aid of a motor into the conical contact device. At this time, the patient's eye is already fixed and stressed by the suction ring and the contact glass in a way which is uncomfortable for the patient. The process of making contact between the suction ring and the laser instrument further increases the stress for the patient, since the process is usually not accomplished entirely smoothly. An additional pressure is therefore exerted at least briefly on the patient's eye, which can be physiologically and psychologically detrimental for the patient.

It is therefore an object of the present invention to provide a remedy in respect of this stress.

SUMMARY

To this end, the invention provides a system having
a laser unit for generating pulsed laser radiation, the pulse length of the laser pulses lying in the femtosecond range,
a hand unit for emitting laser radiation generated by the laser unit, and
a flexible light waveguide for delivering the laser radiation generated by the laser unit to the hand unit.

According to the invention, the laser radiation generated by the laser unit is therefore guided not by means of a rigid free-beam optical connection to the site to be treated; rather, it is guided by means of a flexible light waveguide to a hand unit and is emitted there. The hand unit, connected to the laser unit only via the flexible light waveguide, may be contacted for example with the suction ring or with its coupling device. The hand unit can be configured with a compact size and with a low weight, which on the one hand reduces the psychological stress owing to a substantially smaller unit which is placed onto the eye. At the same time, the actual stress is reduced by facilitated handling and concomitant lower pressure, which is exerted on to the eye. The term "hand unit" is intended here to mean a unit which is configured in respect of its dimensions and its weight so that, for example, it can be guided manually by an operator and for example placed on an eye.

In a preferred embodiment, the laser unit comprises a fibre laser. A fibre laser provides a high beam quality (typically a beam parameter product ≤1.3) with a very compact design.

According to another embodiment, the laser unit and hand unit for the system are connected to one another only by one or more flexible cables, at least one of which comprises the flexible light waveguide. Besides the flexible waveguide, the one or more flexible cables may also comprise for example an electricity supply, a vacuum feed and one or more data lines.

According to another embodiment of the system according to the invention, the hand unit can be positioned independently of the laser unit within the range of mobility of the cable. If the hand unit is comparable in its size to a conventional microkeratome, or is dimensioned only slightly larger, the flap can be produced with comparable stress for the patient with simultaneously increased precision of the cut. The stresses described above, which are associated with a conventional femtosecond laser for the flap production, are therefore reduced.

In this context, in another embodiment according to the invention, the hand unit comprises a coupling instrument which allows mechanical connection to a human eye. The hand unit is either placed directly onto the eye in combination with the suction ring, or is coupled to a suction ring previously fastened on the eye.

In another preferred embodiment of the invention, the laser unit comprises a pulse stretcher for temporal stretching of the laser pulses to pulse lengths of more than 1 picosecond. The pulse stretching makes it possible to reduce the intensity of the laser pulses. Inter alia, reducing the pulse power leads to a lower load for the flexible waveguide.

In this context, it is likewise advantageous for the flexible light waveguide to be a photonic transmission fibre having a large mode area. These light waveguides, also referred to as large mode area fibres (LMA fibres), have core diameters of from 20 µm to more than 40 µm. Owing to the distribution of the light power over a larger area and simultaneous delivery in a low mode order, or in the fundamental mode, LMA fibres make it possible to transmit the laser radiation emitted by the laser unit without degrading the beam parameters of the laser unit, or destroying the LMA fibre by excessively high intensities.

In this regard, it may furthermore be advantageous for at least a part of the flexible light waveguide to cause pulse compression of the pulsed laser radiation generated by the laser unit. This makes it possible for the hand unit to be configured much more compactly. The compression of the laser pulses, which otherwise needs to be carried out in the hand unit, can therefore be relocated to the flexible waveguide and corresponding components in the hand unit can be obviated.

According to an embodiment which is particularly preferred in this regard, the flexible light waveguide is a photonic hollow core fibre. These microstructured optical fibres, also referred to as "photonic crystal fibres" (PCF fibres), contain typically fine capillary structures, filled with air or a gas, in the core or in the cladding region. These structures are so small that the guided light "sees" modified effective material properties of the glass. By varying the spacings of the hole centres and the diameters of the capillary structures, it is possible to control the optical parameters of the fibres and the properties of the light guiding. In particular, the aforementioned pulse compression of the pulsed laser radiation generated by the laser unit can be achieved in this way.

As an alternative, in one embodiment according to the invention the hand unit may comprise compression means for temporal compression of the pulses of the laser radiation. Such compression means may for example comprise an optical grating, preferably a transmission grating.

In one embodiment according to the invention, the hand unit may furthermore have an electro-optical scanner for beam deflection. Such electro-optical crystals for spatially controlling a light beam are usually based on the Pockels or Kerr effect, in which the optical properties of the medium, for instance the refractive index, are modified by applying an electric field to it. In this way, spatial displacement of the light beam can be produced without moving parts. Acousto-optical modulators can also cause rapid and controllable beam deflections by an induced Bragg grating. As an alternative, for example, it is also possible to employ an electro-optical hologram which is produced by recording a volume phase hologram in a liquid crystal monomer mixture, and which generates efficient and controllable beam deflections using external electrical voltages.

The invention furthermore provides a hand unit for emitting pulsed laser radiation generated by a laser unit, having
 a fibre input, through which the laser radiation generated by the laser unit enters the hand unit,
 optics for guiding the laser radiation, and
 a compression instrument for temporal pulse compression of the laser radiation entering through the fibre input and, as an alternative or in addition to the compression instrument, having
 a scanner or an electro-optical crystal for beam deflection of the laser radiation.

The concept according to the invention—i.e. providing a unit for ophthalmology or dermatology which can be moved independently of the laser radiation source, the use of which leads to less stress for the patient—is therefore implemented in a hand unit. The same applies for the hand unit, likewise according to the invention, for emitting pulsed laser radiation generated by a laser unit, wherein the laser radiation has pulse lengths in the femtosecond range.

One of the basic concepts of the present invention is to provide a compact femtosecond laser source, essentially based on fibres, as an easily handleable laser instrument for opthalmological applications. A femtosecond fibre laser is employed as the laser source. It has been found that even pulse energies of approximately 400 nanojoules at 200 kHz are sufficient in order to carry out a very smooth, easily openable flap cut in less than 15 seconds. The fundamental elimination of large-volume power supply units and elaborate active cooling apparatus by using a fibre laser makes it possible to provide a femtosecond LASIK microkeratome with comparable dimensions to a conventional mechanical blade-based microkeratome. It is furthermore proposed that the low pulse energies of less than 1 microjoule, previously stretched to pulse lengths of >1 picosecond, are to be transmitted through transmission fibres with a large mode core without degrading the good beam parameters of the femtosecond laser source or destroying the fibres with large mode diameters by excessively high intensities. The subsequent pulse compression to <500 femtoseconds can then be carried out by miniaturised optical elements in a handpiece. Possible miniature components are a transmission grating for the femtosecond pulse compression and an electro-optical scanner, which functions without moving parts. This beam deflection principle, which is based on the use of an electro-optical crystal, allows entirely sufficient deflection angles of up to 5° in extremely short times of about 1 microsecond. For a wavelength range of from 400 nm to more than 2500 nm, laser beam deflections are therefore possible which, with focused radiation, achieve results that are comparable to a conventional X-Y galvanometer scanner. As an alternative, it is possible to use a so-called photonic fibre with a hollow core, which, with suitable dimensioning, can not only transmit but also compress the picosecond or femtosecond laser pulse. The grating compression in the handpiece can therefore be obviated, and the latter can be made even more compact. This invention provides a femtosecond microkeratome which is suitable as a tool for refractive surgery, in a similarly compact way as the widespread blade-based mechanical microkeratomes.

BRIEF DESCRIPTION OF THE DRAWINGS

The invention will be further explained below with the aid of the appended drawings, in which:

FIG. 2 represents an alternative laser system according to the invention with a simple focusing hand unit for medical application and FIG. 3 represents another exemplary embodiment according to the invention of a laser system with a simple, replaceable glass tip for the contact treatment of opthalmological or other tissues.

DETAILED DESCRIPTION

Figure 1:
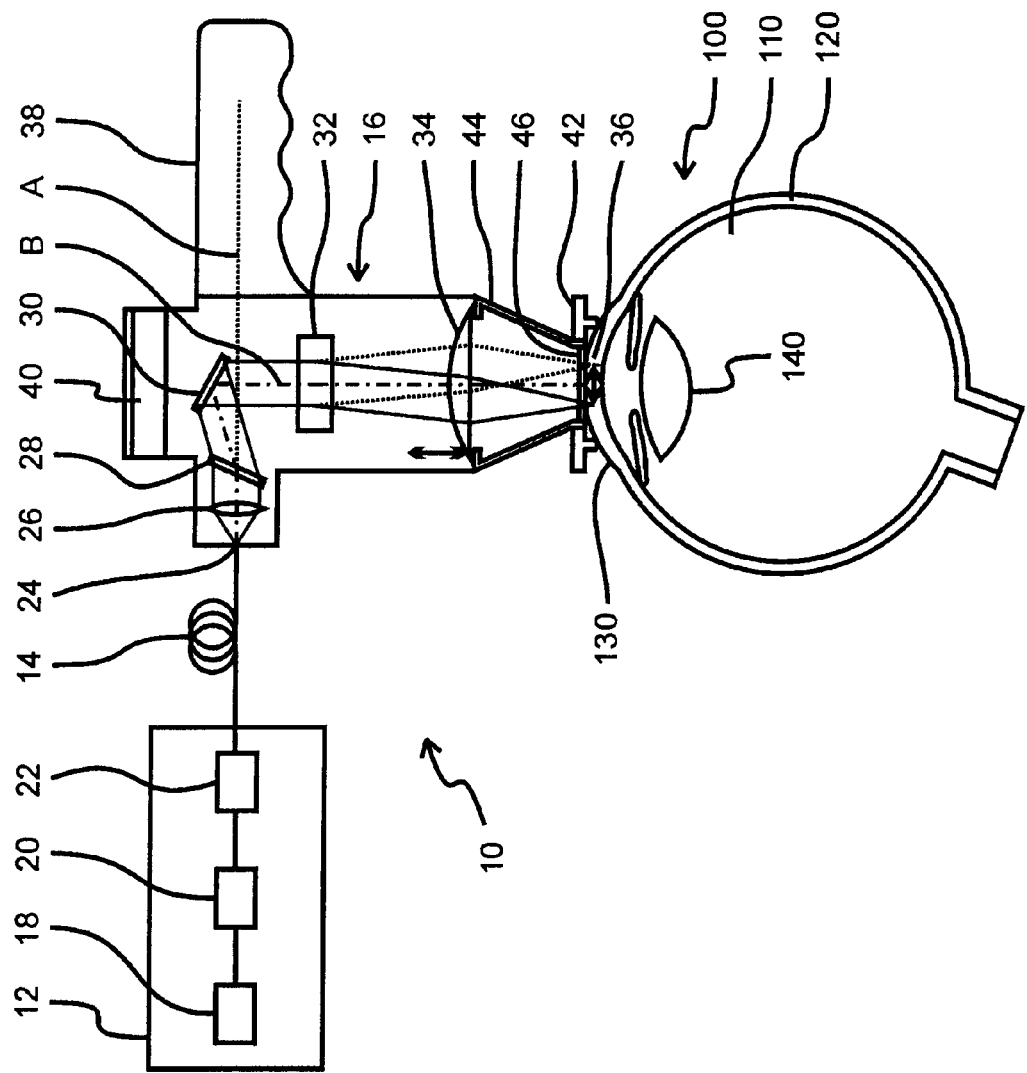
FIG. 1 represents an exemplary embodiment of an opthalmological laser system.

FIG. 1 shows an exemplary embodiment according to the invention of an opthalmological laser system 10. The system has a laser unit 12 and a hand unit 16, which are connected to one another by a cable 14 having a light waveguide. An eye 100 to be treated is furthermore represented schematically in FIG. 1.

The laser unit 12 is a femtosecond laser unit configured as a tabletop instrument, which comprises a femtosecond fibre laser oscillator 18, an amplifier 20 and a pulse stretcher 22. The components of the laser unit may be structurally combined in a single housing as represented in FIG. 1, or formed by two or more separate units which are connected through suitable light waveguides. The fibre laser oscillator 18 operates in a wavelength range of from 1020 nm to 1070 nm. As an alternative, a fibre laser oscillator for the wavelength range of from 1500 nm to 1600 nm could also be used. After the amplifier 20, pulse energies of between 10 nanojoules and >100 nanojoules are provided, typically 300 nanojoules. The pulse length is from 100 femtoseconds to 800 femtoseconds, typically 300 femtoseconds. The repetition frequency for the pulses is from 0.5 MHz to 100 MHz, typically 5 MHz. The pulse stretcher 22 increases the pulse length to values of between 1 picosecond and more than 10 picoseconds.

Connected to the laser unit 12, there is a passive transmission fibre which is fitted in a cable 14 and is configured in the present exemplary embodiment as a so-called LMA fibre (LMA="Large Mode Area"). The core diameter of such fibres is typically between 10 and 50 μm, and the length of the transmission fibre may be between 0.5 m and 2 m. Shorter or much longer versions may, however, also be envisaged. As an alternative, the transmission fibre could also be configured as an active fibre, i.e. the fibre itself functions as an amplification medium for the laser radiation emitted by the laser unit 12. For better handling, the transmission fibre is embedded in a cable which may also comprise electricity, vacuum and/or data lines in addition to the optical waveguide.

The cable 14 establishes a connection between the femtosecond laser unit 12 and the hand unit 16 configured as a treatment handpiece. The housing of the hand unit 16 has a handle 38 and a fibre input 24, through which the pulsed laser radiation generated by the femtosecond laser unit 12 enters the handpiece 16. There, the divergent light beam leaving the transmission fibre is collimated along a first optical axis A by means of a collimator lens 26 and directed onto a transmission grating 28. The transmission grating 28 compresses the laser pulses, which have been stretched by the pulse stretcher 22 in the femtosecond laser unit 12, to the pulse duration of typically 500 femtoseconds or less which is suitable for the opthalmological intervention. The light beam leaving the transmission grating 28 is deviated by a dichroic reflection mirror 30. This serves as a beam splitter: it has a high reflectivity for the wavelength of the femtosecond pulses, whereas it is highly transmissive for the visible spectral range.

The light beam is aligned with an electro-optical deflector 32 by the reflection mirror 30. The electro-optical deflector 32, which is also referred to as a scanner, deflects the incident light beam by up to ±5° as a function of the voltage applied to the deflector, with a response time of approximately 1 microsecond. The electro-optical deflector 32 may on the one hand comprise an electro-optical crystal which operates according to the Kerr principle. As an alternative, it is also possible to use an electro-optical holographic grating which can be generated by recording a volume phase hologram in a liquid crystal monomer mixture. By this holographic technology, switching times of 50-5000 microseconds can be achieved with an angular accuracy of ±3°. In both cases, the electro-optical deflector 32 is transmissive in a wavelength range of from 400 nm to 1600 nm.

The pulsed light beam deflected by the electro-optical deflector 32 is focused by an f-theta objective 34 onto the working plane 36, which is symbolized by a double arrow. By means of the f-theta objective 34, the light beam focus is held in the overall scan field independently of the incidence angle in the working plane 36.

The handpiece 16 has two principal optical axes A and B. The aforementioned first optical axis A is defined by the collimation lens 26 in conjunction with the fibre input 24, and the second is established by the reflection mirror 30 together with the subsequent components detector 32 and f-theta objective 34. In a preferred embodiment, the f-theta objective 34 can be displaced in the direction of the optical axis B in order to allow depth adjustment of the working plane 36 and therefore also three-dimensional shaping of the flap cut.

A CCD camera 40 is furthermore fitted in the handpiece 16. It is arranged along the optical axis B on the same side as the reflection mirror 30, which lies away from the eye 100 being treated. By means of the CCD camera, owing to the transmissivity of all the optical elements along the optical axis B in the visible range, the flap production by means of femtosecond laser pulses can be monitored and optionally controlled in real-time. The housing of the handpiece 16 is provided with a spacer cone 44, which can be coupled to a suction ring 42 fastened on the eye 100. The space cone 44 furthermore comprises an applanation window 46, the function of which will be explained below.

The human eye 100 to be treated is also represented schematically in FIG. 1. The vitreous body 110 is depicted, as well as the sclera 120 lying in the front region of the eye next the cornea 130 to be treated. The lens 140 is furthermore indicated, and the exit of the optic nerve is indicated schematically opposite the lens.

In order to produce a flap cut, the suction ring 42 is initially placed onto the cornea 130 of the eye 100 and aligned, and suction is applied to it. The handpiece 16 is subsequently connected via the spacer cone 44 to the suction ring 42, for example through vacuum suction (not shown). The cornea 130 is thereby pressed against the applanation window 46, so that the cornea 130 is provided with a planar surface approximating the applanation window 46 in the contact region. Optionally, after the coupling, the depth of the incision plane may be set by adjusting the f-theta objective 34 along the optical axis B. The flap cutting is then carried out by means of the pulsed laser radiation generated by the femtosecond laser instrument 12 and guided through the transmission fibre 14 to the handpiece 16. The laser beam is deflected in a suitable way in the working plane 36 by the electro-optical deflector 32, in order to generate the desired cut geometry. Optionally, three-dimensional cut guiding may also be carried out by interaction of the deflector 32 and f-theta objective 34.

FIG. 2 shows an alternative embodiment of the present invention, in the form of a compact femtosecond laser system 200 with a simple focusing handpiece 216 for medical application in ophthalmology or dermatology. The laser source, in the form of a femtosecond laser unit 212, is constructed similarly as the embodiment shown in FIG. 1, i.e. it likewise comprises a laser oscillator 218 for generating laser pulses in the femtosecond range, an amplifier 220 and a pulse stretcher 222. In contrast to the transmission fibre used in FIG. 1, a so-called photonic crystal fibre 214 with a hollow core is used in the embodiment of FIG. 2. Inter alia, this causes temporal pulse compression of the pulses generated and stretched by the laser unit 212. This obviates the need for grating compression in the handpiece 216. The handpiece 216 becomes even more compact, since the pulse compression already takes place in the hollow core fibre 214 which simultaneously functions as a transmission grating. Since the hollow core fibre guides the femtosecond pulse in a glass-free empty space, the fibre is not destroyed even by compressed pulses in the femtosecond range with a high intensity. Besides a collimator lens 226, the handpiece 216 consequently only has a focusing objective 234, which is represented schematically in FIG. 2 by two lenses, in its housing. The light beam emerging from the focusing objective is directed onto tissue 202 to be treated. This may be a skin region or tissue in the eye.

FIG. 3 shows another embodiment of the invention in the form of a femtosecond laser system 300 with a simple, replaceable glass tip for the contact treatment of ophthalmological and other tissue. In respect of the laser source (laser unit 312 with laser oscillator 318, amplifier 320 and pulse stretcher 322) and the transmission fibre 314 (photonic crystal fibre), the embodiment represented in FIG. 3 is similar to that of FIG. 2. In contrast to the embodiment represented in FIG. 2, the embodiment of FIG. 3 has a treatment handpiece 316 equipped with a replaceable "fibre tip" 304, instead of the handpiece 216 provided with imaging optics. This fibre tip 304 consists, for example, of quartz glass—other similar materials such as sapphire may also be envisaged—and forms the termination of the transmission fibre. Its length is for example between 5 and 10 mm, the tip having a diameter of approximately 100 µM. The fibre tip 304 acts as a light-guiding element for the laser radiation of the laser unit 312, which leaves the transmission fibre 314 and is intended to be guided to the front end of the fibre tip 304. The shape of the front end of the fibre tip 304 determines the focal diameter of the laser light on the tissue 302 to be treated. For sterilisation reasons, the fibre tip 304 is replaceable. This embodiment of the invention may for example be used for glaucoma laser treatment, resection of the trabecular tissue in the eye or corneal keratoplasty. The fibre tip 304 may additionally be equipped with a temperature sensor, which signals any unacceptable heating which the treated tissue may experience.

The invention claimed is:

1. A system for ophthalmology or dermatology, comprising:
    a laser source unit having a fiber laser oscillator and amplifier for providing pulsed laser radiation having a pulse length in the femtosecond range, the laser source unit further including a pulse stretcher in optical communication with the fiber laser oscillator and amplifier, the pulse stretcher increasing the pulse length of the pulsed laser radiation to above 1 picosecond;
    a flexible light waveguide optically coupled at a first end to the laser source unit for receiving the pulsed laser radiation having a pulse length above 1 picosecond and guiding the pulsed laser radiation to a second end of the flexible light waveguide; and
    a hand piece coupled to the second end of the flexible light waveguide, the hand piece receiving the pulsed laser radiation from the flexible light waveguide and outputting a focused laser beam, wherein the hand piece includes:
        a transmission grating that compresses the pulse length of the received pulsed laser radiation to the femtosecond range;
        an electro-optical deflector in optical communication with the transmission grating, the electro-optical deflector functioning without moving parts to deflect the received pulsed laser radiation; and
        an f-theta objective in optical communication with the electro-optical deflector, the f-theta objective focusing the pulsed laser radiation deflected by the optical deflector onto a working plane.

2. The system of claim 1, wherein the electro-optical deflector comprises an electro-optical crystal that operates according to the Kerr principle.

3. The system of claim 1, wherein the electro-optical deflector comprises an electro-optical holographic grating.

4. The system of claim 1, wherein the laser source unit and the hand piece are connected to each other exclusively by one or more flexible connection cables, wherein the flexible light waveguide extends in one of the one or more flexible connection cables and wherein a vacuum line extends in one of the one or more flexible connection cables.

5. The system of claim 1, wherein the hand piece includes an interface device for coupling to an eye of a patient to be treated with the focused laser beam.

6. The system of claim 1, wherein the hand piece comprises an interface device for coupling to an eye suction ring.

7. The system of claim 1, wherein the flexible light waveguide is a photonic transmission fibre having a large mode area.

8. The system of claim 1, wherein the flexible light waveguide includes at least a portion effective to cause temporal pulse compression of the pulse laser radiation.

9. The system of claim 8, wherein the flexible light waveguide is a photonic hollow core fibre.

10. The system of claim 1, wherein the hand piece further includes a reflection mirror in optical communication with the transmission grating, the reflection mirror being a beam splitter that directs at least some of the received pulsed laser radiation onto the electro-optical deflector.

11. The system of claim 10, wherein the hand piece further includes a collimator lens in optical communication with the flexible light waveguide and the transmission grating, the collimator lens collimating a divergent light beam of received pulse laser radiation into a collimated light beam directed to the transmission grating.

12. The system of claim 11, wherein the collimator lens collimates the divergent light beam into a collimated light beam along a first optical axis and the reflection mirror directing at least some of the received pulsed laser radiation onto the electro-optical deflector along a second optical axis, the second optical axis being perpendicular to the first optical axis.

13. The system of claim 12, wherein the f-theta objective is adjustable along the second optical axis to allow adjustment of a depth of the working plane.

14. The system of claim 1, wherein the hand piece includes a camera device.

15. A hand piece for use in an ophthalmic or dermatologic laser treatment system, comprising:
    an input interface for coupling to a flexible light waveguide and receiving a pulsed laser beam from the flexible light waveguide;
    a collimator lens in optical communication with the input interface, the collimator lens collimating the received pulse laser beam into a collimated pulsed laser beam along a first optical axis;
    a transmission grating in optical communication with the collimator lens, the transmission grating compressing a pulse length of the pulsed laser beam to the femtosecond range;
    a reflection mirror in optical communication with the transmission grating, the reflection mirror being a beam splitter that directs a portion of the pulsed laser beam in a desired wavelength range along a second optical axis, the second optical axis being perpendicular to the first optical axis;
    an electro-optical deflector in optical communication with the reflection mirror, the electro-optical deflector functioning without moving parts to deflect the portion of the pulsed laser beam directed along the second optical axis; and
    an f-theta objective in optical communication with the electro-optical deflector, the f-theta objective focusing the pulsed laser beam deflected by the optical deflector onto a working plane, wherein the f-theta objective is adjustable along the second optical axis to allow adjustment of a depth of the working plane along the second optical axis.

16. The hand piece of claim 15, wherein the electro-optical deflector comprises at least one of:
    an electro-optical crystal that operates according to the Kerr principle; and
    an electro-optical holographic grating.

* * * * *